(12) United States Patent
Schertiger

(10) Patent No.: US 11,154,688 B2
(45) Date of Patent: Oct. 26, 2021

(54) CATHETER ASSEMBLY WITH A PROTECTIVE SLEEVE INSIDE OF A PACKAGE

(71) Applicant: Coloplast A/S, Humlebaek (DK)

(72) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 425 days.

(21) Appl. No.: 16/092,449

(22) PCT Filed: Apr. 11, 2017

(86) PCT No.: PCT/DK2017/050116
§ 371 (c)(1),
(2) Date: Oct. 10, 2018

(87) PCT Pub. No.: WO2017/178030
PCT Pub. Date: Oct. 19, 2017

(65) Prior Publication Data
US 2019/0105462 A1    Apr. 11, 2019

(30) Foreign Application Priority Data
Apr. 12, 2016    (DK) .......................... PA 2016 70219

(51) Int. Cl.
*A61M 25/01* (2006.01)
*A61M 27/00* (2006.01)
*A61M 25/00* (2006.01)

(52) U.S. Cl.
CPC ...... *A61M 25/002* (2013.01); *A61M 25/0017* (2013.01); *A61M 25/0111* (2013.01); *A61M 27/00* (2013.01)

(58) Field of Classification Search
CPC ................ A61M 25/00; A61M 25/002; A61M 25/0017; A61M 25/0111; A61M 27/00; A61M 2210/1089–1096
See application file for complete search history.

(56) References Cited

U.S. PATENT DOCUMENTS

| 6,065,597 A | 5/2000 | Pettersson et al. |
| 7,476,223 B2 | 1/2009 | McBride |

(Continued)

FOREIGN PATENT DOCUMENTS

| CN | 1222091 A | 7/1999 |
| CN | 1270553 A | 10/2000 |

(Continued)

*Primary Examiner* — Nicholas J Weiss
*Assistant Examiner* — Eric Rassavong
(74) *Attorney, Agent, or Firm* — Coloplast Corp., Coloplast A/S; Nick Baumann

(57) ABSTRACT

A urinary catheter assembly (1) for relieving urinary retention is provided, which comprises a package (3) housing a protective sleeve (5) and a catheter (7), the protective sleeve protecting the catheter. To allow a catheter to be removed from the package with or without a protective sleeve, the catheter assembly forms a removal structure configured for at least a first removal procedure and a second removal procedure. The first removal procedure provides simultaneous removal of the catheter and the protective sleeve from the package with the protective sleeve protecting the catheter, and the second removal procedure provides removal of the catheter from the package and retains the protective sleeve in the package.

8 Claims, 4 Drawing Sheets

(56) References Cited

U.S. PATENT DOCUMENTS

| | | |
|---|---|---|
| 2001/0054562 A1 | 12/2001 | Pettersson et al. |
| 2005/0077200 A1* | 4/2005 | Tippey ............... B65D 83/0805 |
| | | 206/440 |
| 2005/0199521 A1* | 9/2005 | Givens, Jr. .......... A61M 25/002 |
| | | 206/364 |
| 2006/0163097 A1 | 7/2006 | Murray et al. |
| 2006/0196783 A1 | 9/2006 | Bruun et al. |
| 2006/0263404 A1 | 11/2006 | Nielsen et al. |
| 2009/0208368 A1* | 8/2009 | Waldrep ............... A61M 25/002 |
| | | 422/28 |
| 2011/0060317 A1 | 3/2011 | Fröjd |
| 2011/0114520 A1* | 5/2011 | Matthison-Hansen ..................... |
| | | A61M 25/002 |
| | | 206/364 |
| 2011/0120892 A1 | 5/2011 | Frederiksen et al. |
| 2012/0289942 A1 | 11/2012 | Becker et al. |
| 2013/0153446 A1* | 6/2013 | Utas ................... A61M 25/002 |
| | | 206/210 |
| 2013/0261608 A1 | 10/2013 | Tanghoj |
| 2016/0022959 A1 | 1/2016 | Schertiger et al. |
| 2016/0038713 A1 | 2/2016 | Kearns et al. |

FOREIGN PATENT DOCUMENTS

| | | |
|---|---|---|
| CN | 1753702 A | 3/2006 |
| CN | 101132826 A | 2/2008 |
| CN | 103127597 A | 6/2013 |
| CN | 204840604 U | 12/2015 |
| CN | 205084077 U | 3/2016 |
| EP | 2695636 A1 | 2/2014 |
| EP | 2730307 A1 | 5/2014 |
| RU | 2013131785 A | 1/2015 |
| RU | 2580984 C2 | 4/2016 |
| WO | 9741811 A1 | 11/1997 |
| WO | 9806642 A1 | 2/1998 |
| WO | 2011109393 A1 | 9/2011 |
| WO | 2013130459 A1 | 9/2013 |
| WO | 2014074141 A1 | 5/2014 |

* cited by examiner

CATHETER ASSEMBLY WITH A PROTECTIVE SLEEVE INSIDE OF A PACKAGE

TECHNICAL FIELD

Present invention relates to relieving urinary retention and the field of intermittent catheterization.

SUMMARY

A urinary catheter assembly comprising a package housing a protective sleeve and a catheter is provided. The protective sleeve protects the catheter and the catheter assembly forms a removal structure configured for at least a first removal procedure and a second removal procedure. The first removal procedure provides simultaneous removal of the catheter and the protective sleeve from the package with the protective sleeve protecting the catheter. The second removal procedure provides removal of the catheter from the package and retains the protective sleeve in the package.

DETAILED DESCRIPTION OF THE INVENTION

Urinary retention is present in the daily lives of many men, women and children. The problems can typically arise from neurogenic disorders such as spinal cord injury, multiple sclerosis and spina bifida. These conditions may result in paraplegia or tetraplegia (also referred to as quadriplegia). Urinary retention can also be age related, or result from an underlying physical disease, caused by a dysfunction in the bladder.

Relieving urinary retention may involve catheterization with insertion of a urinary catheter into the urethra of the person conditioned with urinary retention. The catheter is often connected to a collecting bag to be mounted on the body and collecting urine from the bladder. The urethra is usually not exposed to external objects and as such it is quite sensitive to exposure to bacteria. Therefore it is important that the part of the catheter being inserted into the urethra is as sterile as possible. Even though the catheter may be sterile in the storage package, the hands of the person inserting the catheter may transfer harmful entities to the catheter when touching it.

One method of lowering the risk of infection associated with intermittent catheterization is to provide the catheter with a protective sleeve. The protective sleeve covers at least part of the insertable part of the catheter right up to the point when it is inserted. This has proven to significantly lower the risk of contamination in catheter users. However, some users find the use of catheters with protective sleeves uncomfortable or otherwise undesirable to use. Removing an undesired protective sleeve from a catheter may be inconvenient. In the case of tetraplegic users, depressed limb functionality and dexterity limitations particularly increases the importance of ease-of-use of catheters for self-catheterization. For this reason, some users prefer to buy and use catheters without protective sleeves.

It is an object to provide a urinary catheter assembly that will enable catheter assembly users to optimize the procedure of removing the catheter from the package and/or the procedure of handling the catheter during insertion. Particularly, it may be an object to vary handling depending on the actual conditions and dexterity of the user.

Accordingly, a urinary catheter assembly comprising a package housing a protective sleeve and an intermittent catheter is provided. The protective sleeve protects the catheter and the catheter assembly forms a removal structure configured for at least a first removal procedure and a second removal procedure, where the first removal procedure provides simultaneous removal of the catheter and the protective sleeve from the package with the protective sleeve protecting the catheter, and the second removal procedure provides removal of the catheter from the package and retains the protective sleeve in the package.

In present context, when the protective sleeve protects the catheter, it is to be understood that the protective sleeve surrounds the catheter so as to cover at least part of the insertable part of the catheter. The insertable part of the catheter most often corresponds to a main tubular part of the catheter. The protective sleeve may cover at least ½ of the insertable part of the catheter when the protective sleeve protects the catheter. The length of the protective sleeve when it protects the catheter is then long enough to minimize the risk of contamination of the catheter when touched. Also, the larger the part of the catheter that is covered by the protective sleeve, the lesser the risk of contamination if the catheter is accidentally brought in contact with a foreign object, for example a sink or a towel in the close vicinity of the user.

The protective sleeve may cover at least ¾ of the insertable part of the catheter when the protective sleeve protects the catheter. The length of the protective sleeve when it protects the catheter is then long enough to further minimize the risk of contamination of the catheter when touched. Also, the risk of contamination is further minimized in relation to the catheter accidentally being brought in contact with a foreign object.

A catheter assembly as described above is able to provide a urinary intermittent catheter with or without a protective sleeve, depending on whether the catheter is removed from the package according to a first removal procedure or according to a second removal procedure, respectively.

The removal structure can be realized by configuring the catheter assembly with one or more attachments between the protective sleeve and the package, and/or one or more attachments between the protective sleeve and the catheter. The attachments could comprise different materials with different specific strengths, similar materials with different geometrical shapes etc. The attachments could also comprise different types of attachments including welded seams, rupturable zones and different kinds of adhesives, e.g. glue between the package and the catheter, e.g. by use of a compound known in the art. Each attachment has an associated detachment force. This detachment force of an attachment depends on the specific structure and composition of the detachment. Accordingly, the attachment material and/or shape and the type and/or amount of attachment glue may be varied to yield a specific detachment force. This enables deliberate design of attachments and associated detachment forces.

In one aspect, one or more attachments may be detachable by hand. This means that the maximum detachment force associated with a particular attachment corresponds to the typical force which can be applied by a human hand.

The attachments could comprise a rupturable zone or a peelable welding of the protective sleeve, the package and/or the catheter. Additionally, the attachments could comprise a piece of cotton, polymer, rubber or any other suitable material attaching the protective sleeve to the package and/or to the catheter.

In the present context, an intermittent urinary catheter is to be understood as a catheter being suitable for use as an intermittent urinary catheter and a catheter assembly user is to be understood as a self-catheterizing person, e.g. a person carrying out catheterisation at home.

Intermittent catheters often have a hydrophilic coating in contrast to indwelling catheters configured for dwelling in the catheter user for periods significantly exceeding the time it takes to empty the bladder. This is because the hydrophilic surface coating of such a catheter is not suitable for indwelling use, in so far as the surface coating tends to stick inside the mucosa of the urethra if left inside the body for a period exceeding 10-20 minutes, due to the hydrophilic coating transforming from being highly lubricious when fully wetted (95% weight water) to being adhesive when the hydration level of the coating is reduced (<75% weight water). Furthermore, indwelling catheters are typically inserted by professionals such as doctors or nurses at hospitals. In such cases, access to means of sterilization are usually readily available. Accordingly, indwelling catheters are generally not provided with protective sleeves. Also for this reason, catheter assemblies as described herein are specifically for intermittent catheters.

Use of a catheter assembly as described above enables postponing urinary catheter users' decision of using a urinary catheter with protective sleeve or without a protective sleeve to the point when the urinary catheter is to be removed from the package. Thus, users are relieved from bringing more than one catheter assembly per catheterization and do not need to decide on protective sleeve usage when buying urinary catheter assemblies. This adds ease and comfort to both the buying and planning process. Additionally, urinary catheter users can bring a single type of urinary catheter assembly and choose to use it with protective sleeve or without protective sleeve depending on e.g. access to soap and clean water, gloves or on other factors present when the urinary catheter is to be inserted. Furthermore, the urinary catheter providing company may only manufacture and promote one type of urinary catheter assembly, which may save manufacturing, handling and promotion costs of the company manufacturing, handling and/or promoting the urinary catheter assembly.

Furthermore, removing an undesired protective sleeve from a catheter may be inconvenient. In the case of tetraplegic users, depressed limb functionality and dexterity limitations particularly increases the importance of ease-of-use of catheters for self-catheterization. For this reason, some users prefer to buy and use catheters without protective sleeves.

In summary, a catheter assembly as described may provide ease and comfort for users while lowering costs associated with providing the catheter assembly.

The catheter assembly may further comprise a first attachment between the protective sleeve and the package, and a second attachment between the catheter and the protective sleeve, the first attachment defining a first detachment force (A) and the second attachment defining a second detachment force (B), and the first and second attachments may be designed such that the protective sleeve is detached from the package and remains attached to the catheter when the catheter is removed from the package according to the first removal procedure, and such that the protective sleeve is detached from the catheter and remains attached to the package, when the catheter is removed from the package according to the second removal procedure.

The removal structure can be realized by configuring the catheter assembly with one or more attachments between the protective sleeve and the package, and/or one or more attachments between the protective sleeve and the catheter. The attachments could be configured so that removing the catheter from the catheter assembly according to at least one of the removal procedures causes one or more of said attachments to break before the catheter is completely removed. That is, removing the catheter according to the first removal procedure may cause the first attachment between the protective sleeve and the package to detach before the catheter is completely removed from the package. The detachment force (B) of the second attachment attaching the protective sleeve and the catheter is then sufficient to maintain the protective sleeve being attached to the catheter. This causes the catheter to be removed from the package with the protective sleeve attached to the catheter. Similarly, removing the catheter according to the second removal procedure may cause the second attachment between the protective sleeve and catheter to be detached. In this case, the detachment force (A) of the first attachment is sufficient to maintain the catheter attached to the package and the catheter is removed from the package without a protective sleeve. The attachments could comprise a rupturable zone or a peelable welding of the protective sleeve, the package and/or the catheter. Additionally, the attachments could comprise a piece of cotton, polymer, rubber, metal or any other suitable material attaching the protective sleeve to the package and/or to the catheter.

The removal structure may comprise means for performing a predefined structural modification of at least one of the intermittent urinary catheter, the package, the protective sleeve, the first attachment, and the second attachment, wherein the predefined structural modification defines the removal procedure to be either the first removal procedure or the second removal procedure.

In this case, the removal procedure is defined to be the first or the second removal procedure by the chosen predefined structural modification. As such, the role of the predefined structural modification is to shift the balance of forces acting between the protective sleeve and the package and the forces acting between the protective sleeve and the catheter. In one case, the predefined structural modification may cause the magnitude of forces attaching the protective sleeve to the catheter to exceed the magnitude of the forces attaching the protective sleeve to the package. This defines the removal procedure to be the first removal procedure. In another case, the predefined structural modification may cause the magnitude of forces attaching the protective sleeve to the package to exceed the magnitude of the forces attaching the protective sleeve to the catheter. This defines the removal procedure to be the second removal procedure. The catheter assembly may also be pre-configured with the balance of forces being shifted towards attaching the protective sleeve more firmly to the package than to the catheter or vice versa. That is the catheter assembly may be pre-configured for the first or second removal procedure if no predefined structural modification is performed. In this case, the predefined structural modification is only performed if the removal procedure is to be changed from the pre-configured removal procedure.

The means for performing the predefined structural modification may comprise a user operable element configured to detach at least one of the first and second attachments.

In case the protective sleeve is attached to the package by a first attachment and to the catheter by a second attachment as described above, the predefined structural modification comprises detaching the first or second attachment. The predefined structural modification may detach the first attachment leaving the protective sleeve attached to the catheter by the second attachment. This defines the removal procedure to be the first removal procedure. The predefined structural modification may also detach the second attachment leaving the first attachment intact. This defines the removal procedure to be the second removal procedure.

The detachment force (A) of the first attachment may also be greater than the detachment force (B) of the second attachment. In this case, the predefined structural modification comprises detaching the first attachment. This defines the removal procedure to be the first removal procedure and the catheter is removed with the protective sleeve protecting the catheter. If the predefined structural modification is not performed, the second attachment at one point breaks. This causes the catheter to be removed without the protective sleeve and the removal procedure is defined to be the second removal procedure. Similar arguments may be construed if the balance of the detachment forces was oppositely shifted.

The catheter assembly may further comprise at least a third attachment between the protective sleeve and the package, the third attachment defining a third detachment force (C).

In this case, the protective sleeve is attached to the package by a first attachment defining a first detachment force (A), the protective sleeve is additionally attached to the catheter by a second attachment defining a second detachment force (B), the protective sleeve is further attached to the package by a third attachment defining a third detachment force (C). This allows for a more versatile configuration of attachments and associated detachment forces.

The sum of the first detachment force (A) and the third detachment force (C) may be larger than the second detachment force (B), and the second detachment force (B) may be larger than the third detachment force (C). According to this embodiment, the combined detachment force of the first and third attachments (A+C) attaching the protective sleeve to the package is larger than the second detachment force (B) attaching the protective sleeve to the catheter. Also, the second detachment force (B) is larger than the third detachment force (C).

Removing the catheter according to the first removal procedure may at one point detach the first attachment arranged to attach the protective sleeve to the package before the catheter is completely removed from the package, e.g. by use of the means to perform a predefined structural modification. At this point, the second attachment arranged to attach the protective sleeve to the catheter and the third attachment arranged to attach the protective sleeve to the package remain. As the second detachment force (B) is larger than the third detachment force (C), removing the catheter from the package will detach the third attachment and retain the second attachment. The second attachment attaches the protective sleeve to the catheter and thus the protective sleeve remains attached to the catheter when the catheter is removed from the package. Thus, removing the catheter according to the first removal procedure will cause the catheter to be removed from the package with the protective sleeve.

Removing the catheter from the package according to the second removal procedure may at one point put strain on the first, second and third attachment simultaneously. As the combined detachment force of the first and third attachments (A+C) attaching the protective sleeve to the package is larger than the second detachment force (B) attaching the protective sleeve to the catheter, the second attachment at one point is detached. Thus, the catheter is removed without the protective sleeve when the catheter is removed from the package according to the second removal procedure.

As described above, the attachments may be in the form of different materials with different specific strengths or similar materials with different geometrical shapes. The attachments could also comprise different types of attachments including welded seams and rupturable zones. Also, the protective sleeve can be attached adhesively, e.g. glued to the package and/or to the catheter by use of a compound known in the art.

The attachments may be configured so that the sum of the first detachment force (A) and the third detachment force (C) is between 1.1 and 1.9 times the second detachment force (B), and wherein the second detachment force (B) is between 1.1 and 1.9 times the third detachment force (C).

According to this embodiment, it is ensured that the combined detachment force of attachments attaching the protective sleeve to the package is 1.1 to 1.9 times larger than the detachment force of the attachment attaching the protective sleeve to the catheter. Additionally, it is ensured that after the first attachment is detached, the detachment force (B) of the second attachment attaching the protective sleeve to the catheter is 1.1 to 1.9 times larger than the detachment force (C) of the third attachment attaching the protective sleeve to the package. Accordingly, consistent removal of the catheter with or without protective sleeve according to the chosen removal procedure may be ensured.

In another embodiment, the sum of the first detachment force (A) and the third detachment force (C) is between 1.6 and 1.9 times the second detachment force (B), and the second detachment force (B) is between 1.6 and 1.9 times the third detachment force (C). In this case, even more consistent removal of the catheter with or without protective sleeve according to the chosen removal procedure may be ensured.

In another embodiment, the sum of the first detachment force (A) and the third detachment force (C) is between 1.8 and 1.9 times the second detachment force (B), and the second detachment force (B) is between 1.8 and 1.9 times the third detachment force (C). In this case even more consistent removal of the catheter with or without protective sleeve according to the chosen removal procedure may be ensured.

The means for performing the predefined structural modification may comprise a user operable element configured to detach the first attachment. In this case, the first attachment may be detached by a user operating the user operable element. When the first attachment is detached, the protective sleeve is more firmly attached to the catheter than to the package. Accordingly, operating the user operable element in this case causes the catheter to be removed from the package with the protective sleeve protecting the catheter. The user operable element may be any structure in mechanical connection with the first attachment configured to be grabbed by a user. The user operable element may be, e.g., a string of a flexible material, a pre-cut slit of the package configured to be pulled open by a user, a part of the package configured to be grabbed by a user etc.

In another embodiment, the first attachment with detachment force (A) is provided by a peelable welding, the second attachment with detachment force (B) is provided by a peelable welding and the third attachment with detachment force (C) is provided by a rupturable zone of the protective sleeve.

By providing the attachments in accordance with present embodiment, the attachments are provided in a manner ensuring optimum compatibility with catheter assembly manufacturing methods known in the art. In case the catheter assembly comprises a user operable element configured to detach the first attachment, the user operable element is configured to detach a peelable welding according to this embodiment. This allows for a simple mechanical connection between the user operable element and the peelable welding.

In another embodiment the first attachment with detachment force (A) is provided by a rupturable zone of the protective sleeve, the second attachment with a detachment force (B) is provided by a peelable welding and the third attachment with detachment force (C) is provided by a peelable welding.

By providing the attachments in accordance with present embodiment, the attachments are provided in a manner ensuring optimum compatibility with catheter assembly manufacturing methods known in the art. In case the catheter assembly comprises a user operable element configured to detach the first attachment, the user operable element is configured to detach a rupturable zone according to this embodiment. This allows for a simple mechanical connection between the user operable element and the rupturable zone of the protective sleeve. Furthermore, detaching the rupturable zone of the protective sleeve by means of the user operable element provides increased control over the rupture of the rupturable zone.

In another embodiment, the catheter comprises a hydrophilic surface layer configured to reduce surface friction upon swelling with a liquid medium. The hydrophilic surface layer may be provided in a hydrophilic material such as polyvinylidone or polyvinylpyrrolidone. The hydrophilic material may be applied to a surface of the catheter by a manufacturing process known in the art. The hydrophilic surface may provide increased comfort and less chance of damaging the urethra in relation to insertion of the catheter in the urethra. The urinary catheter assembly may be provided with the liquid medium stored in the package housing.

The liquid medium may be provided in a compartment for the liquid medium separated from the catheter. In that case the liquid medium is confined in said compartment in a liquid state until intended use of the catheter. In this case, the urinary catheter assembly may be configured so that at least one of the first and second opening procedures releases some or all of the fluid medium to provide contact between said fluid medium and the surface of the catheter. The liquid medium may also be provided so that at least the insertable part of the catheter is stored in the liquid medium. By providing the catheter assembly with the liquid medium stored in the package, catheter users are relieved from applying a liquid medium to the hydrophilic surface layer after the catheter is removed from the package.

The package may comprise antibacterial fluids such as hydrogen peroxide. In the case of hydrogen peroxide, it is advantageous to make sure the hydrogen peroxide does not make contact with the hydrophilic surface layer as hydrogen peroxide may chemically react with the hydrophilic coating. Additionally, the catheter assembly may comprise medicaments such as lidocaine to be brought in contact with the urethra or bladder.

The protective sleeve may be stored in the package in a storage position near a connector of the catheter, and removing the catheter from the package according to the first removal procedure may result in the protective sleeve being extended to a use-position in which the protective sleeve protects the catheter.

According to this embodiment, the protective sleeve is stored in a storage position in which it is compressed in the length direction to be stored near the connector. In use-position, the protective sleeve is pulled down over the catheter so that it covers at least half of the insertable part of the catheter.

According to this embodiment, when removing the catheter from the package according to the first removal procedure, an attachment attaching the protective sleeve to the package extends the protective sleeve to protect the catheter before the attachment is detached and the catheter is removed from the package.

The protective sleeve in the storage position may be pre-folded into a concertina pleated configuration. The pre-folded configuration may be made in a material without any particular demand for flexibility. If the material has no pre-folds and needs to be folded, then the material needs a certain flexibility.

By storing the protective sleeve in a storage position near the connector of the catheter, the hydrophilic surface of the catheter is wetted particularly well by the fluid in the catheter assembly. Furthermore, because the protective sleeve is extended when the catheter is removed from the package according to the first removal procedure, extension of the protective sleeve requires no effort besides removing the catheter from the package.

In another embodiment, the catheter substrate comprises at least one material selected from the group of: thermoplastic elastomeric materials, other thermoplastic materials, curable elastomeric materials, polyamide resins, elastomers or any mixture thereof.

The catheter substrate may be provided in a relatively strong and durable material such as a thermoplastic elastomeric material, other thermoplastic materials, curable elastomeric materials, polyamide resins, elastomers or any mixture thereof, i.e. the group may comprise materials like, poly vinyl chloride (PVC), polyurethane (PU) and/or latex.

The urinary catheter assembly may be configured with a width of the protective sleeve being between 1-15 mm larger than a diameter of the insertable part of the catheter. In preferred embodiments, said diameter difference may be 0.1 mm to 1 mm, 1 mm to 5 mm, 2 mm to 8 mm, 3 mm to 10 mm. The diameter difference is preferably chosen to ensure mobility of the protective sleeve relative to the insertable part of the catheter.

Other embodiments relate to a urinary catheter assembly comprising a package housing a protective sleeve and an intermittent urinary catheter, the protective sleeve protecting the catheter, wherein the catheter assembly comprises a first attachment between the protective sleeve and the package, and a second attachment between the catheter and the protective sleeve, wherein the catheter assembly further comprises at least a third attachment between the protective sleeve and the package, said third attachment being separate from said first attachment.

In further embodiments, a method of removing a catheter from a catheter assembly is provided, the catheter assembly comprising a package, a protective sleeve and a catheter, wherein the catheter assembly is configured so that removing the catheter from the package according to a first removal procedure results in the protective sleeve to be removed from the package along with the catheter, and so that removing the catheter from the package in a second manner results in the catheter being removed without the protective sleeve, the method comprising the steps of:
  selecting between removing the catheter from the package according to the first removal procedure or removing the catheter according to the second removal procedure, and removing the catheter from the package according to the first or second removal procedure.

The step of removing the catheter from the package may comprise a step of opening the package according to a first opening procedure or according to a second opening procedure, wherein opening the package according to the first opening procedure results in the protective sleeve being removed from the package along with the catheter, and wherein opening the package according to the second opening procedure results in the catheter being removed without the protective sleeve. This provides a method for removing a catheter with or without a protective sleeve from the catheter assembly. Moreover, a single catheter assembly may provide a catheter with or without a protective sleeve increasing the ease and comfort of self-catheterization.

The step of removing the catheter from the package according to the first and/or second removal procedure may comprise performing a predefined structural modification of at least one of the intermittent urinary catheter, the package, the protective sleeve, a first attachment, and a second attachment according to the selected removal procedure.

In this case, the predefined structural modification defines the removal procedure to be the first or the second removal procedure. There may be one predefined structural modification that defines the removal procedure to be the first removal procedure and another that defines the removal procedure to be the second removal procedure. The predefined structural modification may also be configured so that removing the catheter according to the first removal procedure comprises performing the predefined structural modification and removing the catheter according to the second removal procedure does not comprise performing the predefined structural modification and vice versa.

Allowing a user to define the removal procedure by a predefined structural modification provides the user with a well defined distinction between the first and second removal procedure. This may increase the reliability of the removal procedures while possibly also providing more convenient handling of the catheter assembly.

The predefined structural modification may comprise operating a user operable element configured to detach at least one of a first and second attachments. In this case, the removal procedure is defined by detaching the first attachment between the protective sleeve and the package or detaching the second attachment between the protective sleeve and the catheter. This provides an even more reliable and convenient method of removing the catheter from the catheter assembly according to the first or the second removal procedure.

The predefined structural modification according to the first removal procedure may comprise pulling the user operable element along a first direction, and performing the predefined structural modification according to the second removal procedure may comprise pulling the user operable element along a second direction. In this case, the user operable element may be operated in two distinct ways defining the removal procedure to be either the first or the second allowing convenient operation of the user operable element.

Performing the predefined structural modification according to the first removal procedure may comprise operating a first user operable element, and performing the predefined structural modification according to the second removal procedure may comprise operating a second user operable element. Individual user operable elements for use in the first or second removal procedure allows for clear distinction between the first and second removal procedure.

According to an embodiment, a method of removing a catheter from a catheter assembly is provided, wherein the protective sleeve is attached to the package by a first attachment with a first detachment force (A), the protective sleeve is additionally attached to the catheter by a second attachment with a second detachment force (B), the protective sleeve is further attached to the package by a third attachment with a third detachment force (C), and the sum of the first detachment force (A) and the third detachment force (C) is larger than the second detachment force (B), and the second detachment force (B) is larger than the third detachment force (C), and wherein performing the predefined structural modification according to the first removal procedure will break the first attachment between the package and the protective sleeve, and performing the predefined structural modification according to the second removal procedure will leave all three attachments intact.

BRIEF DESCRIPTION OF THE DRAWINGS

Embodiments will now be described in further detail with reference to the accompanying drawings in which.

DETAILED DESCRIPTION OF THE DRAWINGS

It should be understood that the detailed description and specific examples, while indicating embodiments, are given by way of illustration only, since various changes and modifications within the spirit and scope of the invention will become apparent to those skilled in the art from this detailed description.

Figure 1:
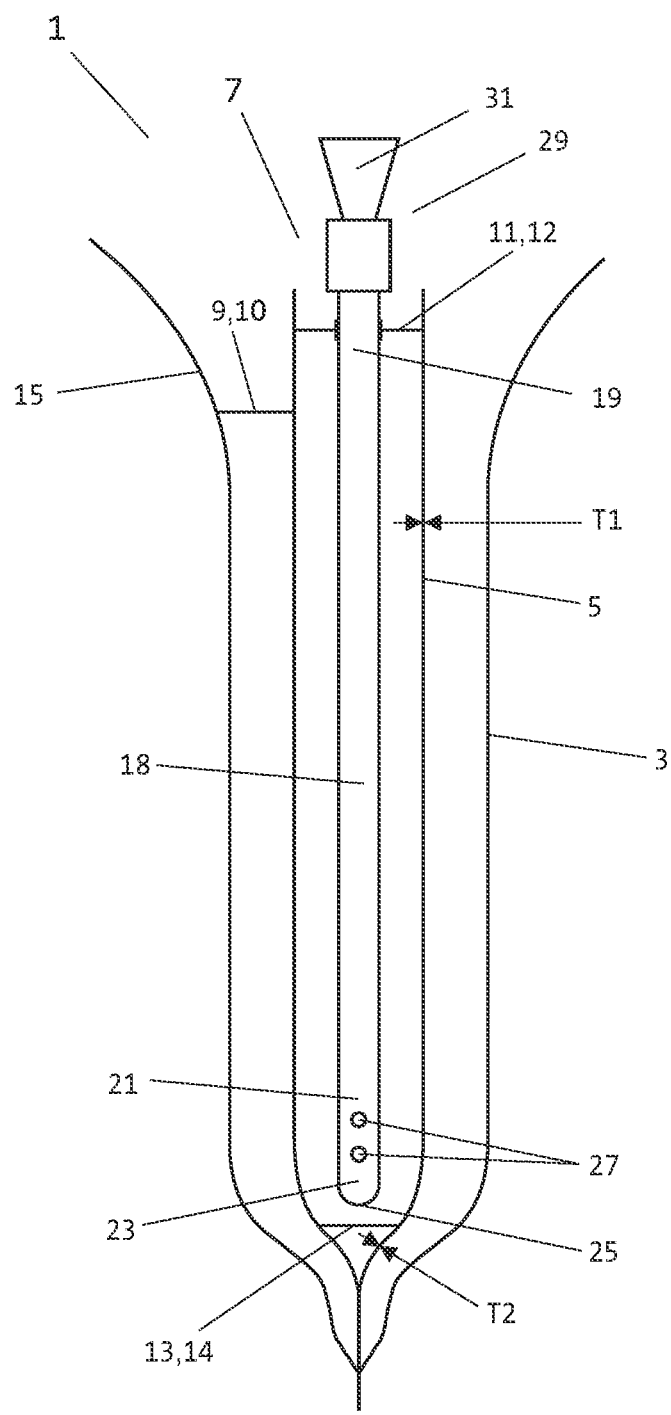
FIG. 1 illustrates a urinary catheter assembly according to an embodiment.

FIG. 1 illustrates a urinary catheter assembly 1 comprising a package 3 housing a protective sleeve 5 and a catheter 7, the protective sleeve 5 protecting the catheter 7. The catheter assembly 1 forms a removal structure and the removal structure comprises three attachments 9, 11 and 13. Moreover, the protective sleeve 5 is attached to the package 3 by the first attachment 9 with detachment force (A) and a third attachment 13 with detachment force (C). Additionally, the protective sleeve 5 is attached to the catheter 7 by the second attachment 11 with detachment force (B). The attachments 9, 11 and 13 are manufactured so that the sum of the first detachment force (A) and the third detachment force (C) is 1.9 times the second detachment force (B), and so that the second detachment force (B) is 1.9 times the third detachment force (C). It then follows that A=2.61 C and C=0.38 A. It is thus ensured that the combined detachment force (A+C) of attachments 9 and 13 attaching the protective sleeve 5 to the package 3 is significantly larger than the detachment force (B) of the attachment 11 attaching the protective sleeve 5 to the catheter 7. Additionally, it is ensured that after the first attachment 9 is detached, the detachment force (B) of the second attachment 11 attaching the protective sleeve 5 to the catheter 7 is significantly larger than the detachment force (C) of the third attachment 13 attaching the protective sleeve 5 to the package 3. Accordingly, consistent removal of the catheter 7 with or without protective sleeve 5 according to the chosen removal procedure is ensured.

In the embodiment illustrated in FIG. 1, the first attachment 9 with detachment force (A) is provided by a peelable welding 10, the second attachment 11 with a detachment force (B) is provided by a peelable welding 12 and the third attachment 13 with detachment force (C) is provided by a rupturable zone 14 of the protective sleeve. The rupturable zone 14 is realized by manufacturing the protective sleeve 5 material (thickness T1) with a reduced thickness (T2) in said rupturable zone 14 during manufacturing.

Figure 2:
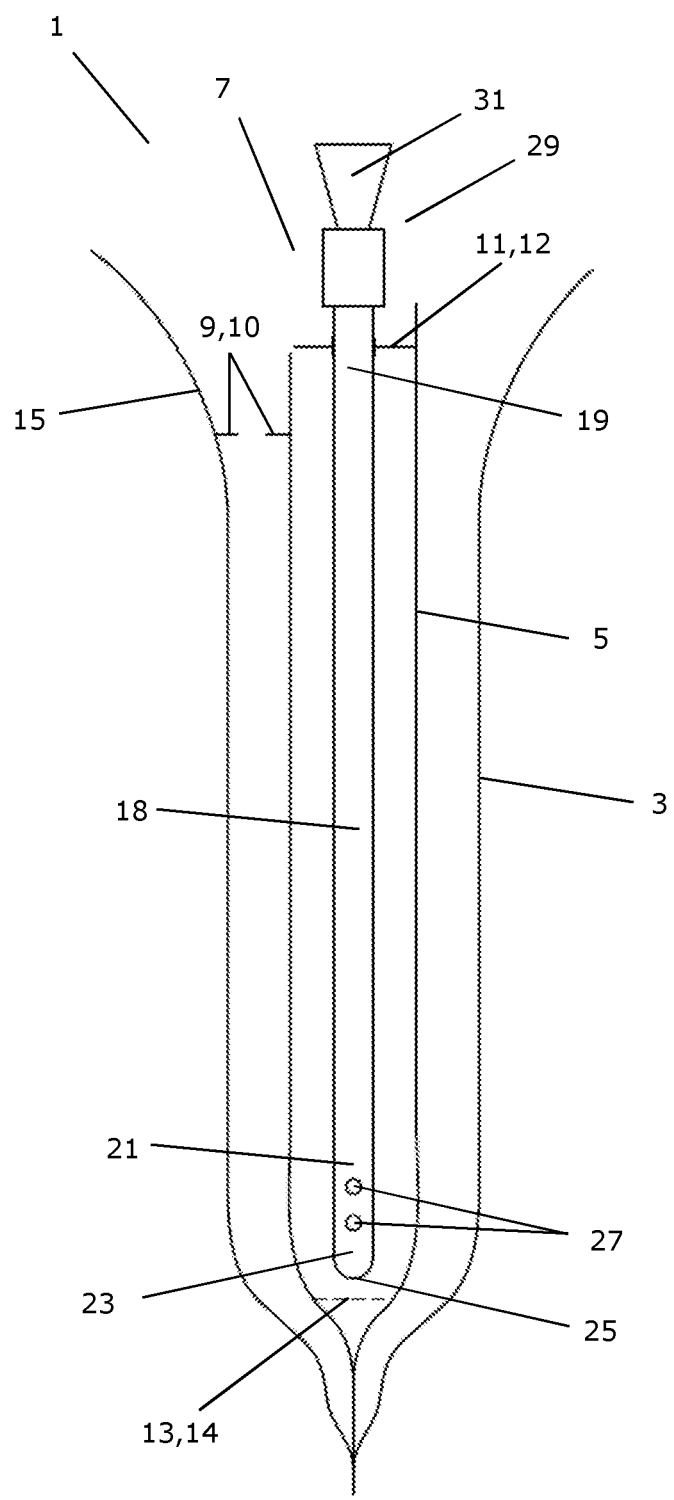
FIG. 2 illustrates a urinary catheter assembly according to an embodiment.
Figure 3:
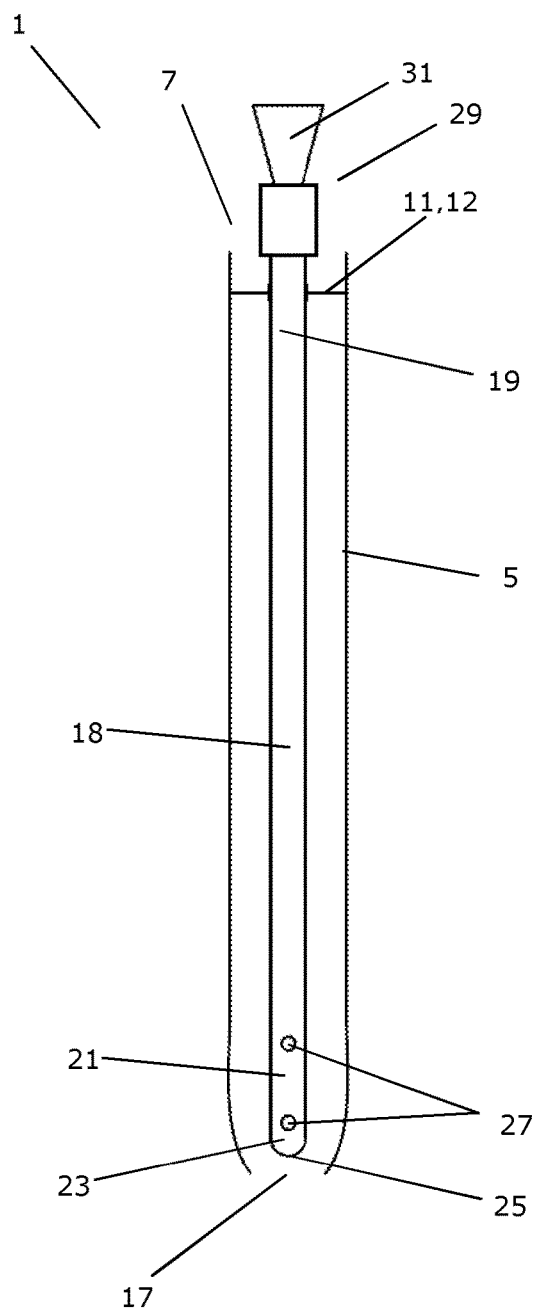
FIG. 3 illustrates a urinary catheter with a protective sleeve according to an embodiment.

Removing the catheter 7 according to a first removal procedure comprises operating a user operable element 15 in mechanical connection with the first attachment (9,10). Operating the user operable element 15 causes the first attachment (9,10) to be detached as illustrated in FIG. 2. After the first attachment (9,10) is detached, the second attachment (11,12) arranged to attach the protective sleeve 5 to the catheter 7 and the third attachment (13,14) arranged to attach the protective sleeve 5 to the package 3 remain. As the second detachment force (B) is larger than the third detachment force (C), removing the catheter 7 from the package 3 will detach the third attachment (13,14) and retain the second attachment (11,12) providing removal of the catheter 7 with the protective sleeve 5 protecting the catheter 7. Thus, removing the catheter 7 according to the first removal procedure will cause the catheter 7 to be removed from the package 3 with the protective sleeve as shown in FIG. 3. Note that detaching the rupturable zone 14 of the protective sleeve 5 ruptures the protective sleeve 5 in a controlled manner leaving the protective sleeve 5 with an opening 17. The protective sleeve 5 may then easily be retracted during insertion of the catheter 7.

Figure 4:
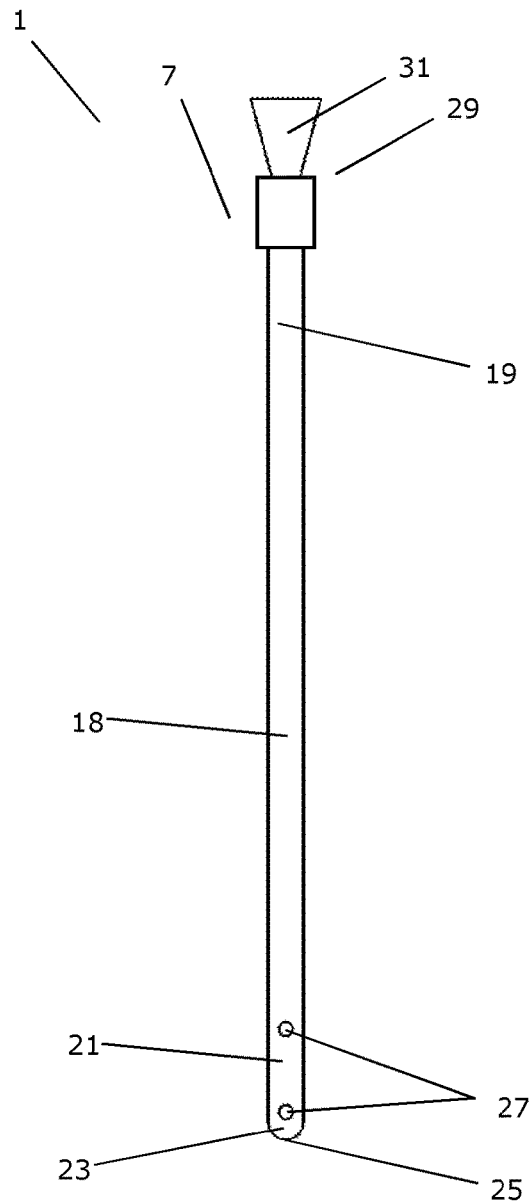
FIG. 4 illustrates a urinary catheter without a protective sleeve according to an embodiment.

Removing the catheter 7 from the package 3 according to a second removal procedure at one point puts strain on the first (9,10), second (11,12) and third (13,14) attachments simultaneously. The combined detachment force of the first (9,10) and third attachments (13,14) (A+C) attaching the protective sleeve 5 to the package 3 is larger than the second detachment force (B) attaching the protective sleeve 5 to the catheter 7. This causes the second attachment (11,12) at one point to be detached while the first (9,10) and third (13,14) attachments retain the protective sleeve 5 attached to the package 3. Thus, the catheter 7 is removed without the protective sleeve 5 as shown in FIG. 4 when the catheter 7 is removed from the package 3 according to the second removal procedure.

Figure 5:
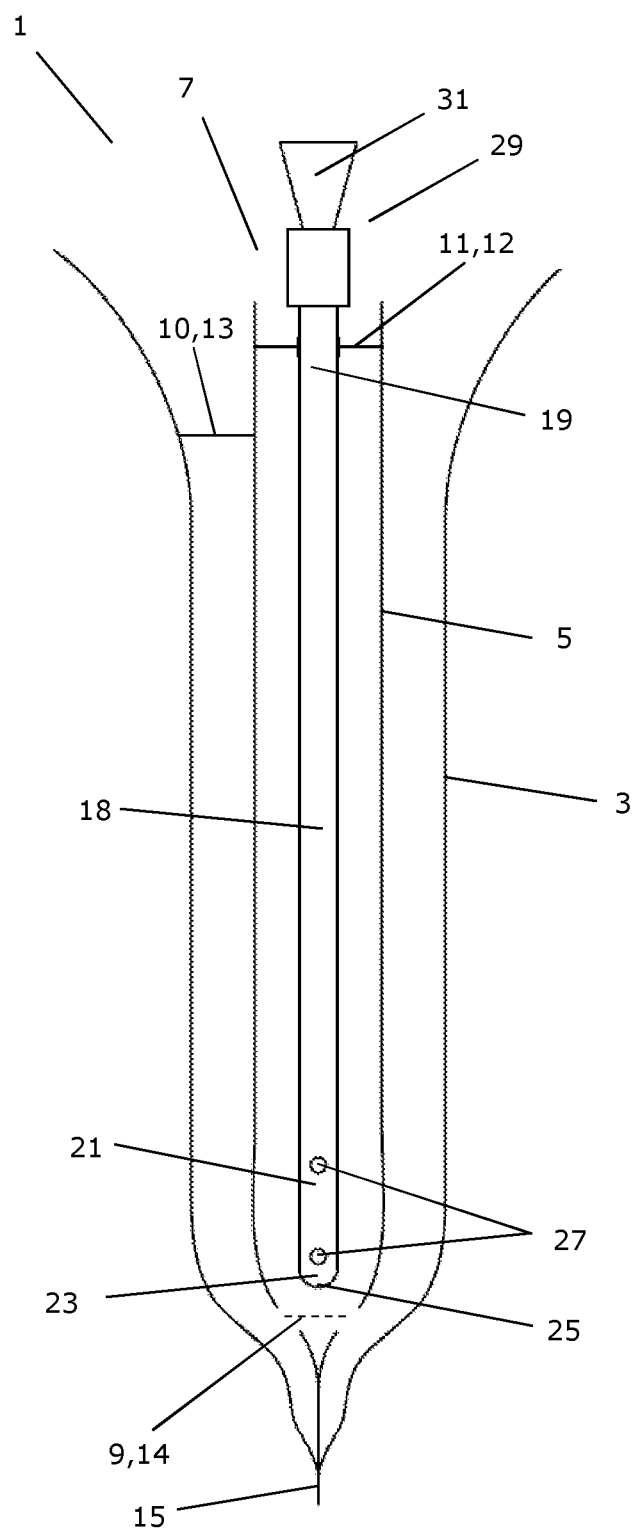
FIG. 5 illustrates a urinary catheter assembly according to an embodiment.

In an alternative embodiment shown in FIG. 5, the first attachment 9 with a first detachment force (A) is provided by a rupturable zone 14 of the protective sleeve 5, the second attachment 11 with a second detachment force (B) is provided by a peelable welding 12 and the third attachment 13 with a third detachment force (C) is provided by a peelable welding 10. The relative magnitudes of the first detachment force (A), the second detachment force (B) and the third detachment force (C) are the same as described above. According to this embodiment, the user operable element 15 is configured to detach the first attachment 9 in the form of the rupturable zone 14. To remove the catheter 7 from the package 3 according to the first removal procedure, the first attachment (9,14) is detached by operating the user operable element 15. The sleeve 5 is then attached to catheter 7 by the second attachment (11,12) and to the package 3 by the third attachment (10,13). Because the second detachment force (B) is larger than the third detachment force (C), the catheter 7 is then removed from the package 3 with the protective sleeve 5 protecting the catheter 7 as shown in FIG. 3.

Removing the catheter 7 according to the second removal procedure does not comprise operating the user operable element 15. Conversely, during the second removal procedure, strain is simultaneously put on the first (9,14), second (11,12) and third (10,13) attachments. The relative magnitudes of their detachment forces at one point causes the second attachment (11,12) to be detached and the catheter 7 is removed from the package 3 without the protective sleeve 5 as illustrated in FIG. 4.

The catheter 7 comprises a main tubular part 18 extending from a distal end 19 to a proximal end 21. A tip 23 is positioned in the proximal end 21 of the catheter 7 and is provided as a rounded closed end 25 of the tube constituting the main tubular part 18 of the catheter 7. Eyelets 27 for letting urine enter into the catheter 7 is typically positioned close to the tip 23. A connector 29 is arranged in the distal end 19 and comprises a flared end 31 of the catheter 7 so that the diameter of the connector 29 increases with respect to the main tubular part 18.

The catheter 7 is between size eight FR and size eighteen FR. FR (or French size or Charriere (Ch)) is a standard gauge for catheters approximately corresponding to the outer circumference in mm. More accurately, the outer diameter of the catheter in mm corresponds to FR divided by three. Thus eight FR corresponds to a catheter with an outer diameter of 2.7 mm and eighteen FR corresponds to a catheter with an outer diameter of 6 mm.

The invention claimed is:

1. A urinary catheter assembly comprising:
    an intermittent urinary catheter including a tube extending from a closed proximal end to a distal end;
    a connector attached to the distal end of the intermittent urinary catheter;
    a protective sleeve, with the intermittent urinary catheter inserted into the protective sleeve, and the protective sleeve connected to one of the tube and the connector by a first peelable weld;
    a liquid medium stored in the protective sleeve in contact with the tube; and
    a package, with the protective sleeve and the intermittent urinary catheter inserted into the package, and the package is connected to the protective sleeve by a second peelable weld and a rupturable zone, with the rupturable zone coupled to the protective sleeve along a proximal portion of the protective sleeve at a location distal of the second peelable weld;
    wherein removal of the package from the protective sleeve ruptures the rupturable zone and forms an outlet opening at the proximal portion of the protective sleeve that is adapted to allow the liquid medium to drain out of the protective sleeve;
    wherein protective sleeve has a first thickness measured at a distal portion of the protective sleeve, and a second thickness of the protective sleeve measured in the rupturable zone at the proximal portion of the sleeve is less than the first thickness.

2. The urinary catheter assembly of claim 1, wherein the package is adapted for removal from the protective sleeve by breaking the second peelable weld and the rupturable zone, and the breaking of the rupturable zone forms the outlet opening at the proximal portion of the protective sleeve.

3. The urinary catheter assembly of claim 1, wherein:
    1) the second peelable weld is adapted to release the package from the protective sleeve with a first detachment force (A), 2) the rupturable zone is adapted to rupture along the proximal portion of the protective sleeve with a third detachment force (C), 3) the first peelable weld is adapted to release the protective sleeve from one of the tube and the connector with a second detachment force (B), and a sum of the first detachment force (A) and the third detachment force (C) is larger than the second detachment force (B).

4. The urinary catheter assembly of claim 3, wherein the second detachment force (B) is larger than the third detachment force (C).

5. The urinary catheter assembly of claim 3, wherein the sum of the first detachment force (A) and the third detachment force (C) is between 1.1 and 1.9 times the second detachment force (B), and wherein the second detachment force (B) is between 1.1 and 1.9 times the third detachment force (C).

6. The urinary catheter assembly of claim 1, wherein the first peelable weld is distal the second peelable weld, and the second peelable weld is distal the rupturable zone.

7. The urinary catheter assembly of claim 1, wherein the intermittent urinary catheter includes a hydrophilic coating.

8. A urinary catheter assembly comprising:
   an intermittent urinary catheter including a tube extending from a closed proximal end to a distal end;
   a connector attached to the distal end of the intermittent urinary catheter;
   a protective sleeve, with the intermittent urinary catheter inserted into the protective sleeve, and the protective sleeve connected to one of the tube and the connector by a first peelable weld; and
   a package, with the protective sleeve and the intermittent urinary catheter inserted into the package, and the package is connected to the protective sleeve by a second peelable weld and a rupturable zone, with the rupturable zone coupled to the protective sleeve along a proximal portion of the protective sleeve at a location distal of the second peelable weld;

wherein:

1) the second peelable weld is adapted to release the package from the protective sleeve with a first detachment force (A), 2) the rupturable zone is adapted to rupture along the proximal portion of the protective sleeve with a third detachment force (C), 3) the first peelable weld is adapted to release the protective sleeve from one of the tube and the connector with a second detachment force (B), wherein removal of the package from the protective sleeve is configured to form a drain opening at the rupturable zone whereby a sum of the first detachment force (A) and the third detachment force (C) is between 1.1 and 1.9 times the second detachment force (B), and the second detachment force (B) is between 1.1 and 1.9 times the third detachment force (C).

* * * * *

UNITED STATES PATENT AND TRADEMARK OFFICE
CERTIFICATE OF CORRECTION

PATENT NO. : 11,154,688 B2
APPLICATION NO. : 16/092449
DATED : October 26, 2021
INVENTOR(S) : Lars Olav Schertiger It is certified that error appears in the above-identified patent and that said Letters Patent is hereby corrected as shown below:

In the Claims

In Column 12, Line 54, in Claim 1, delete "protective sleeve" and insert -- the protective sleeve --, therefor.

Signed and Sealed this
Twenty-eighth Day of June, 2022

Katherine Kelly Vidal
*Director of the United States Patent and Trademark Office*